United States Patent [19]

Ohya et al.

[11] Patent Number: 4,869,111
[45] Date of Patent: Sep. 26, 1989

[54] CYCLIC FATIGUE TESTING APPARATUS

[75] Inventors: Kanji Ohya, Komaki; Kohji Ogura, Ohgaki, both of Japan

[73] Assignee: NGK Spark Plug Co., Ltd., Japan

[21] Appl. No.: 252,392

[22] Filed: Oct. 3, 1988

[30] Foreign Application Priority Data

Oct. 2, 1987 [JP] Japan .................................. 62-250208
Nov. 20, 1987 [JP] Japan .................................. 62-294468

[51] Int. Cl.$^4$ .............................................. G01N 3/32
[52] U.S. Cl. ......................................... 73/811; 73/812; 73/813
[58] Field of Search ................. 73/811, 810, 812, 813, 73/814, 815; 310/328, 329, 330, 338

[56] References Cited

U.S. PATENT DOCUMENTS 2,936,612  5/1960  Mason ............................... 73/813 X

FOREIGN PATENT DOCUMENTS

2060179  4/1981  United Kingdom ................. 73/811

Primary Examiner—Jerry W. Myracle
Attorney, Agent, or Firm—Larson & Taylor

[57] ABSTRACT

A cyclic fatigue testing apparatus intended for testing the cyclic fatigue of samples such as ceramic or the like, in which it comprises a vibration plate assembly comprising a flex plate provided with piezoelectric element layer(s) on at least one surface thereof, a sample supporting member disposed on the vibration plate for supporting the sample and a loading member for forcing the samnple onto the supporting member. The apparatus can operate over a wide frequency range by adjusting the position of the sample supporting member with respect to the flex plate and selecting the frequency of an alternating voltage to be applied to each piezoelectric element layer.

11 Claims, 7 Drawing Sheets

CYCLIC FATIGUE TESTING APPARATUS

FIELD OF THE INVENTION

The present invention relates to a cyclic fatigue testing apparatus for measuring the mechanical strength of samples such as ceramic.

BACKGROUND OF THE INVENTION

In the cyclic fatigue testing of the mechanical strength of samples such as ceramic or the like there is known a three point bending test apparatus in which one surface of the sample to be tested is supported at two points thereof, the other surface is supported at the center portion thereof and a bending fatigue of the sample is measured by applying a dynamic load on the either side thereof. An apparatus generally used for such fatigue testing typically comprises a linear reciprocating mechanical actuator mechanism such as a piston and a cylinder as an impact source for applying the dynamic load on the either side of the sample.

U.S. Pat. No. 4,572,011 discloses such a linear reciprocating mechanical actuator mechanism comprising a hydraulic actuator and a servo mechanism.

With the known testing apparatuses, it is complicated to control or adjust a driving force to be applied to the sample being tested so that the intended accuracy in determining the load can be attained. Also, the conventional cyclic fatigue testing apparatus have disadvantages that they can not generate a high frequency driving force, the operation of them is noisy, and there may easily occur an abrasion or wear due to a mechanical friction, leading to make it difficult to maintain the test conditions constant during the test procedure.

Further, the problem arises in the known apparatuses that it is difficult to operate them with sufficient accuracy and thus it may result in that the test sample is exposed to harmful overloads which influence the fracture behaviour and the measured results in a non-acceptable way.

Furthermore, with the conventional system using a magnetic or hydraulic actuator which has a speed of response of the order of mm sec, it is impossible to generate a vibration having a high frequency cycle of 100 Hz or more.

Therefore, an object of the present invention is to provide a cyclic fatigue testing apparatus intended for testing the cyclic fatigue of samples such as ceramic or the like, which can eliminate the above-mentioned disadvantages.

It is a further object of the present invention to provide a cyclic fatigue testing apparatus conveniently used for test samples having very low strength.

SUMMARY OF THE INVENTION

According to one aspect of the present invention, there is provided a cyclic fatigue testing apparatus for testing the cyclic fatigue of samples such as ceramic, comprising a vibration plate assembly having a flexible plate provided with a piezoelectric element layer on at least one surface thereof, at least one end portion of said flexible plate being secured to a stationary table, a supporting member mounted on the bending surface of said vibration plate assembly for supporting the sample, and means for forcing the sample onto the supporting member.

Preferably, the flexible plate of the vibration plate assembly may be secured to the table at one end portion and may be provided with a weight at the other end portion.

Alternatively, the flexible plate of the vibration plate assembly may be secured to the table at the both end portions which have outwardly extended edges on which the weights are mounted, respectively.

Preferably, the stationary table may be provided with elastic supporting means for compensating any overload applied by the loading means to the sample.

According to another aspect of the present invention, there is provided a cyclic fatigue testing apparatus for testing the cyclic fatigue of samples such as ceramic, comprising a vibration plate assembly having a flexible plate provided with a piezoelectric element layer on at least one surface thereof, at least one end portion of said flexible plate being secured to a stationary table, a supporting member for supporting the sample, means for liftably retaining said sample supporting member, an elastic strip member for interconnecting said sample supporting member and the bending surface of said vibration plate assembly, and means for forcing the sample onto said sample supporting member.

Preferably, the elastic strip member has one end secured to the bending surface of said vibration plate assembly and the other end connected to the underside of the sample supporting member through an interconnecting rod which passes through a hole provided in the retaining means.

BRIEF DESCRIPTION OF THE DRAWINGS

The invention will now be described in detail hereinafter, by way of example, with reference to the accompanying drawings in which.

DETAILED DESCRIPTION OF THE PREFERRED EMBODIMENTS

Figure 1:
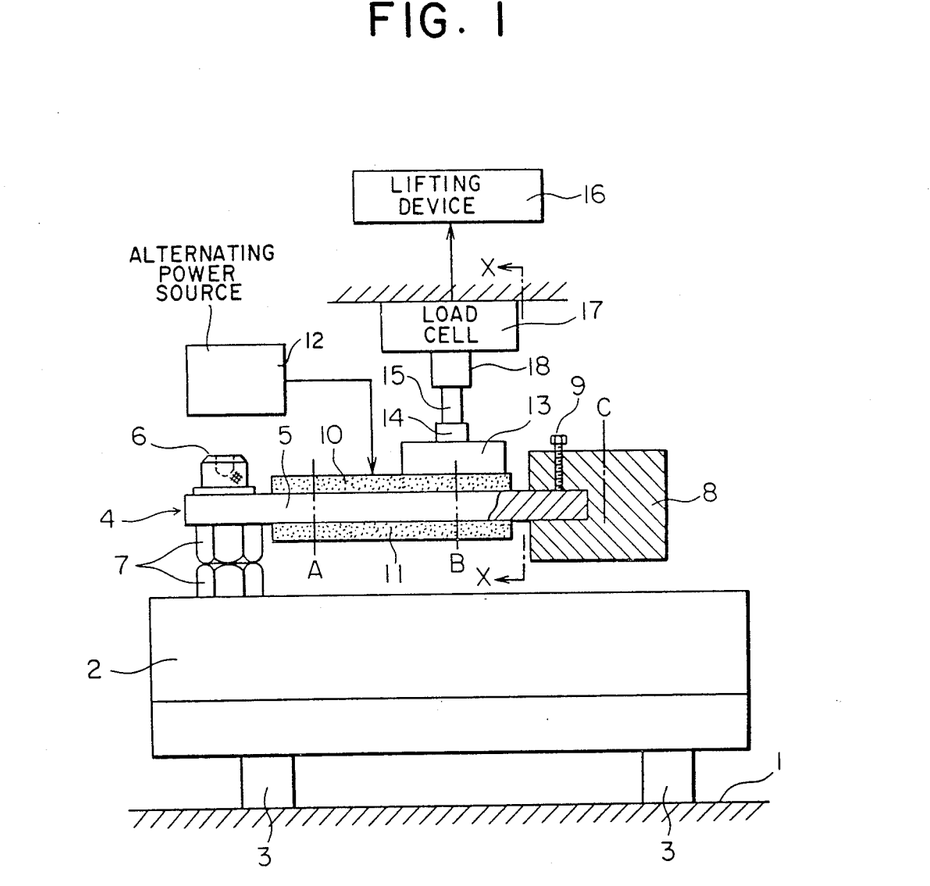
FIG. 1 is a schematic sectional view showing a first embodiment of the present invention.
Figure 2:
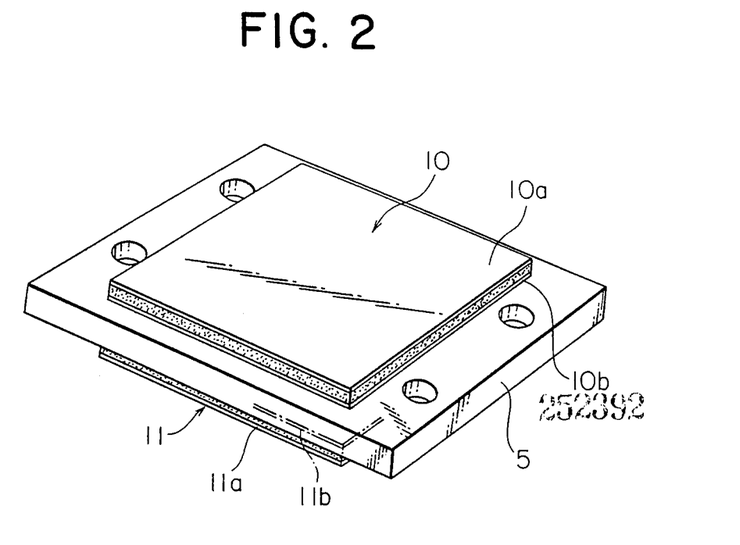
FIG. 2 is a perspective view of a vibration plate assembly in the apparatus shown in FIG. 1.
Figure 3:
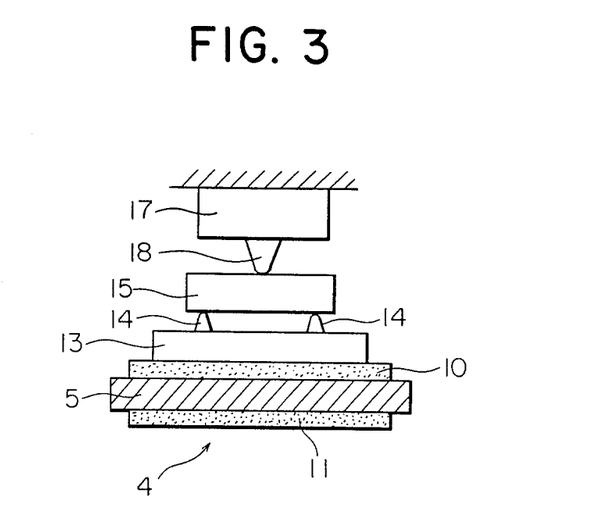
FIG. 3 is a longitudinal sectional side view taken along a line X—X of FIG. 1.

Referring now to FIGS. 1 to 3, there is illustrated a first embodiment of a cyclic fatigue testing apparatus according to the present invention.

Reference numeral 1 denotes a suitable base provided for supporting the cyclic fatigue testing apparatus according to the present invention. On the base 1 is semi-floatingly disposed a table 2 via elastic supporting members 3 which may be made of a soft rubber, a sponge, a metal spring or other elastic materials. On the table 2 is mounted vibration plate assembly 4 of a bimorph structure of an impact source in such a manner that it is horizontally overhung. This vibration plate assembly 4 comprises a flexible plate 5 of a rectangular shape having one end portion which is fastened to the table 2 by two supporting studs (only one of which is designated by reference numeral 6) and nuts 7, and the other opposite end portion on which a weight 8 is mounted by bolts (only one of which is designated by reference numeral 9). The flexible plate 5 is provided with piezoelectric ceramic element layers 10 and 11 at each surface thereof. The piezoelectric ceramic element layers 10 and 11, as shown in FIG. 2, are provided with electrodes 10a and 10b (11a and 11b) at both side, respectively, and are polarized in opposite direction to each other. The outer electrodes 10a and 11a of the piezoelectric ceramic element layers 10 and 11 are connected to an alternating power source 12, and the inner electrodes 10b and 11b are earthed through the flexible plate 5. The piezoelectric ceramic element layers 10 and 11 are so arranged that one of them is extended and the other is contracted when a voltage is applied thereto.

On the intermediate portion of the vibration plate assembly 4 is provided a sample supporting member 13 which, as shown in FIG. 3, is provided with two supporting pieces 14 transversely spaced at the upper surface thereof. These supporting pieces 14 are intended to receive a sample 15 such as ceramic, glass, metal and plastic.

Above the vibration plate assembly 4 there is provided a lifting device 16 from which a load cell 17 is suspended. The load cell 17 is provided with a sample pushing piece 18 adapted to make contact with the upper surface of the sample 15 at the intermediate position between the supporting pieces 14.

In using the apparatus to perform tests, a suitably prepared sample 15 is placed on the supporting pieces 14 of the sample retaining member 13, and the load cell 17 is lowered by means of the operation of the lifting device 16 until the pushing piece 18 comes into contact with the sample 15. In this way, the sample 15 is supported in three points. In this connection, if the lowering of the load cell 17 exceeds slightly the level for which it is intended, the elastic supporting members 3 fixed on the underside of the table 2 are compressed so that the table 2 and then the vibration plate assembly 4 are displaced downwards thereby retaining the sample 5 at a constant pressure without any damage.

On this condition, to the piezoelectric ceramic element layers 10 and 11 is applied an alternating voltage having a predetermined frequency of a pulse wave, a sinusoidal wave or a triangular wave from the source 12. Therefore, a strain shall occur in the piezoelectric ceramic element layers 10 and 11, and thus a bending vibration shall occur in the vibration plate assembly 4 because the other end portion thereof is retained by the inertia force of the weight 8. By this bending vibration the sample retainers 14 are upwards and downwards displaced to push the either end portion of the underside of the sample 15, thereby resulting in a bending strain being periodically applied to the sample 15 with center at the point corresponding to the sample pushing piece 18. In this way, the sample 15 becomes fatigued by the application of the dynamic load, thereby finally resulting in a crack being formed in the sample 15. By measuring the time when the crack is formed, the applied voltage, the number of the pulses or other parameters, it is possible to determine the resistance of the sample against a breaking, that is the structural strength of the sample.

To show how the amplitude of the vibration in the sample 15 may be changed with respect to the position thereof on the vibration plate assembly 4, experiments were carried out on the illustrated apparatus with the sample retaining member 13 being positioned on each of three positions designated generally by A, B and C and a voltage having a peak-to-peak value of 300 V being applied to the piezoelectric ceramic element layers 10 and 11.

When the sample retaining member 13 was placed at the position A, the frequency and the amplitude in the sample were 157.9 Hz and 54.3 Kg p-p, respectively. At the position B, the frequency was 230.8 Hz and the amplitude was 44.1 Kg p-p. At the position C, the frequency 339.0 Hz and the amplitude 11.0 Kg p-p.

It can be understood from these experiments that the amplitude of vibration in the sample is varied in response to the position of the sample retaining member 13 and becomes maximum at the position A. It is therefore possible to adjust the amplitude of the vibration to which the sample is subjected by changing the mounting position of the sample retaining member 13.

In the preceding description, it has been indicated that the flexible plate 5 was rectangularly shaped, however other shapes may be used.

Figure 4:
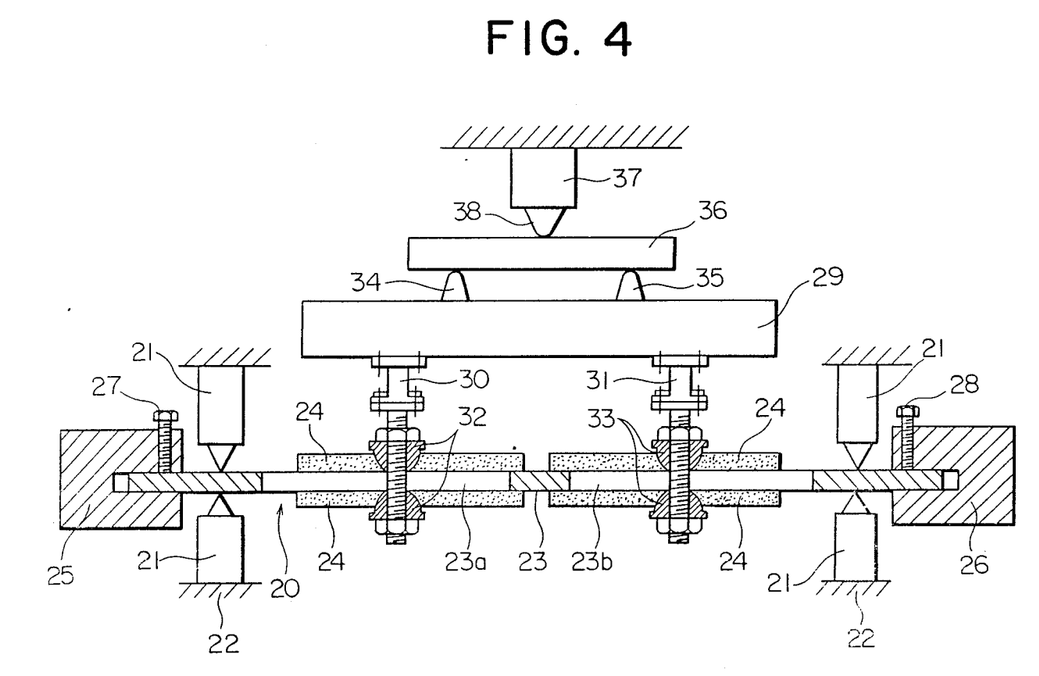
FIG. 4 is a schematic sectional view showing a second embodiment of the present invention.
Figure 5:
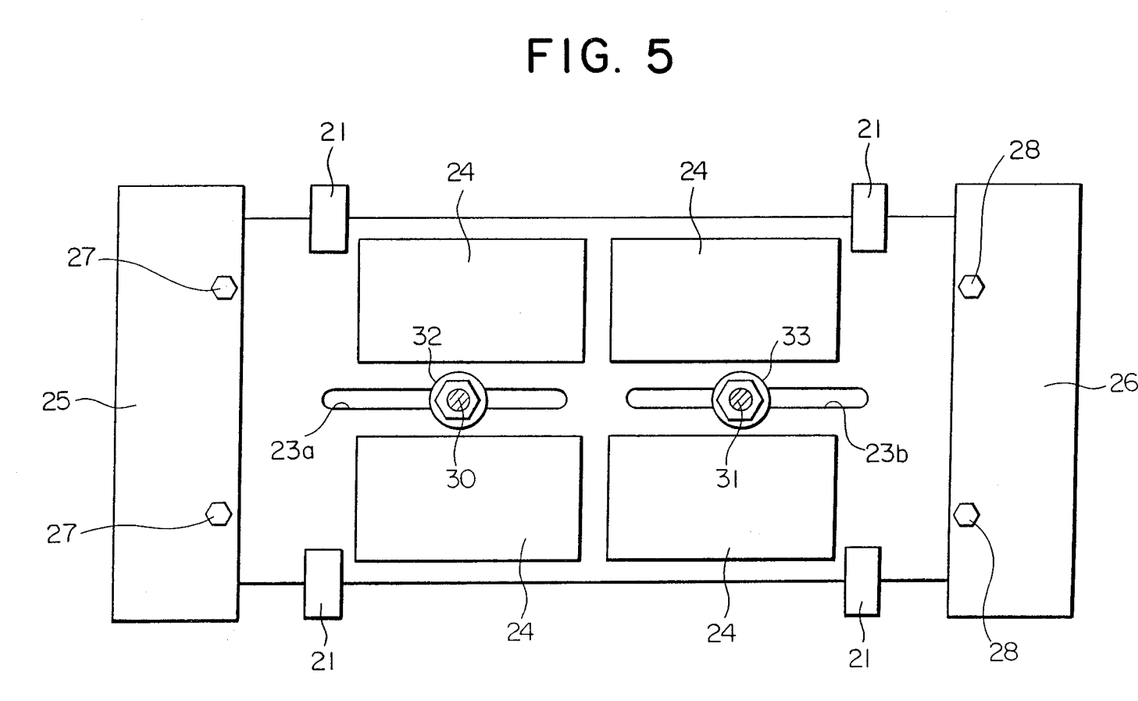
FIG. 5 is a plan view of the essential portion of the embodiment shown in FIG. 4.

FIGS. 4 and 5 illustrate a second embodiment of the present invention.

A vibration plate assembly 20 is supported by eight supporting members 21 fixed on a base 22 at points corresponding node points of a vibrating. The vibration plate assembly 20 comprises a flexible plate 23 of a rectangular shape having two slots 23a and 23b along the center axis thereof, and four piezoelectric ceramic element layers 24 adhered to the both surfaces along the respective slots 23a and 23b, each layer on the either surface being spaced from the others. On the opposite end portions there are removably mounted weights 25 and 26 by screws 27 and 28, respectively.

Each of the slots is intended slidably support a sample retaining member 29 via elastic rod members 30 and 31, and slidable pieces 32 and 33 so that the sample retaining member 29 may be horizontally displaced along the slots 23a and 23b. On the upper surface of the sample retaining member 29 are mounted two, front and rear, supporting edges or pieces 34 and 35 on which a sample 36 to be tested is placed. Above the sample retaining member 29 is suspended a load cell 37 which is provided with a sample pushing piece 38 being adapted to make contact with the upper surface of the sample 36 at the point corresponding to the intermediate position between the supporting pieces 34 and 35.

With the illustrated arrangement, when the intermediate position between the supporting pieces 34 and 35 is set at the position corresponding to the center position of the flexible plate 23 by moving the sample retainer 29 along the slots 23a and 23b, the sample 36 may be subjected to a maximum amplitude of vibration, and it is therefore possible to control the amplitude of the vibration to which the sample 36 is subjected by moving the sample retainer 29 along the slots 23a and 23b.

In use, the cyclic fatigue testing is begun by putting the sample 36 on the supporting pieces 34 and 35 of the sample retaining member 29 and applying an alternating voltage to the piezoelectric element layers 24. A bending vibration occurred in the piezoelectric element layers 24 is transmitted to the sample 36 through the supporting pieces 34 and 35 and thus a bending strain vibration shall occur in the sample 36 so that the sample 36 shall be vibrated as a fulcrum which is positioned corresponding to the position to the pushing piece 38. Therefore, the sample 36 becomes fatigued and may finally be broken. When the both end portions of the flexible plate 23 are provided with the weights 25 and 26, the bending vibration occurred in the sample 36 may be increased by an inertia force of the respective weight. With the bending of the flexible plate 23 the slidable pieces 32 and 33 fixed to the slots 23a and 23b may be subjected to a transverse relative stress, but such a transverse stress or strain can be adsorbed by the elastic rods 30 and 31.

Figure 6:
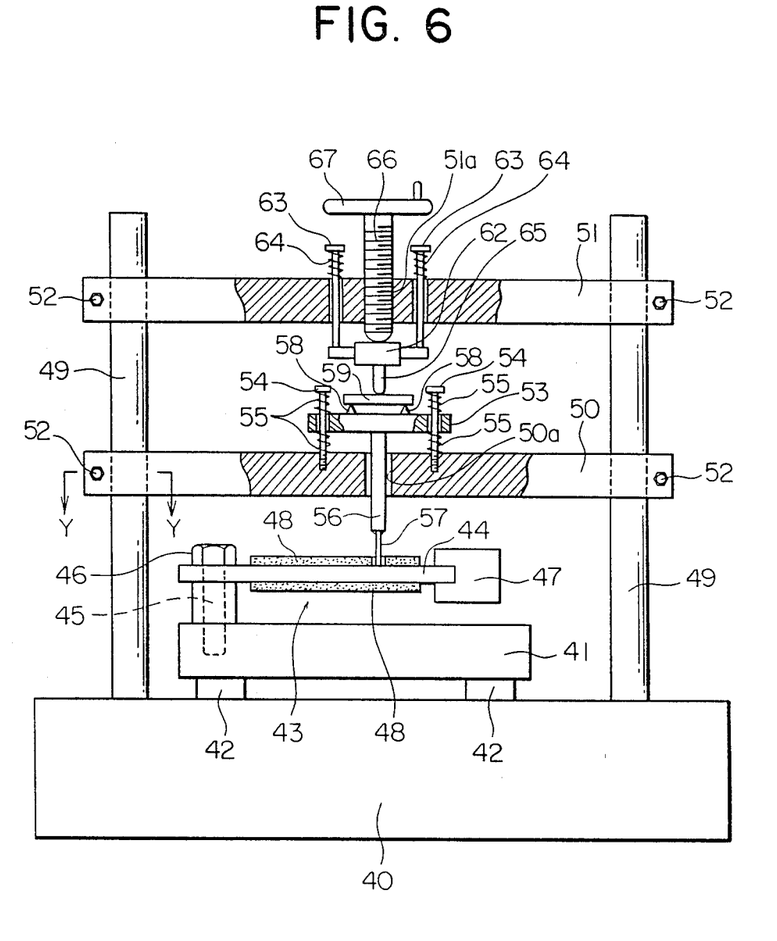
FIG. 6 is a schematic partial sectional elevation of a third embodiment of the present invention.

Turning to FIG. 6, there is shown a third embodiment of the present invention in which the apparatus comprises a base 40 on which a table 41 is semi-floatingly disposed via elastic supporting members 42. The elastic supporting members 42 may be made of a soft rubber, a sponge, a metal spring or other elastic material. The apparatus also comprises a vibrating plate assembly 43 of a bimorph structure which behaves as an impact source, and includes a flexible plate 44 of a rectangular shape. One end portion of the flexible plate 44 is mounted on the table 41 by two fastenings (only one being designated by reference numberal 45) and nuts 46, and the other opposite end portion thereof is provided with a weight 47 so that the flexible plate 44 may be horizontally arranged like a cantilever. On the both surfaces of the flexible plate 44 there are provided piezoelectric element layers 48. Each of the piezoelectric element layers 48 may be provided with electrodes at both side and polarized similarly to that shown in FIG. 2. The outer electrodes of the piezoelectric element layers 48 are connected to an alternating power source not shown, and the inner electrodes are grounded through the flexible plate 44. The piezoelectric element layers 48 are so arranged that one of them is extended and the other is contracted by application of a voltage.

Figure 7:
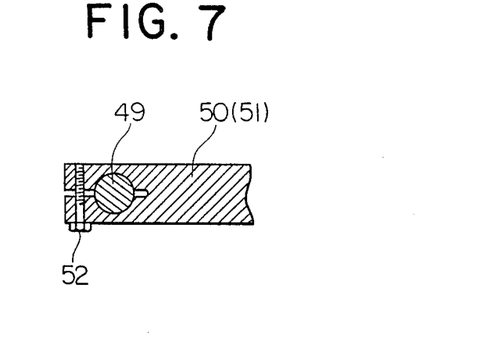
FIG. 7 is a section taken along a line Y—Y of FIG. 6.

On the base 40 are vertically provided pillars 49 to which a lower frame 50 and an upper frame 51 are fixed by screws 52. That is, as shown in FIG. 7, each end portion of the respective frame is bifurcated, fitted on the associated pillar 49, and movably fastened thereon by the screw 52.

The lower frame 50 is provided with a vertical through hole 50a which is positioned with respect to the position of a desired bending surface of the vibration plate assembly 43. A sample supporting member 53 is provided over the hole 50a. The sample supporting member 53 is floatingly mounted on the lower frame 50 via two studs 54 and springs 55 fitted thereon, and at the underside is provided with an interconnecting rod 56 which downward extends through the hole 50a. To the lower end of the rod 56 is welded one end of an elastic strip 57 which may be formed of a leaf spring having small spring constant. The opposite end of the strip 57 is adapted to make contact with the flexible plate 44.

The sample supporting member 53 is provided with two supporting pieces 58 spaced at the upper surface thereof. These supporting pieces 58 are adapted to receive a sample 59 to be tested.

It will be appreciated that the elastic strip 57 should be designed so that it can transmit a dynamic load from the flexible plate 44 to the sample 59 without snapping or breaking.

The coupling of the elastic strip 57 to the flexible plate 44 may practically be performed in the following manner.

Figure 8:
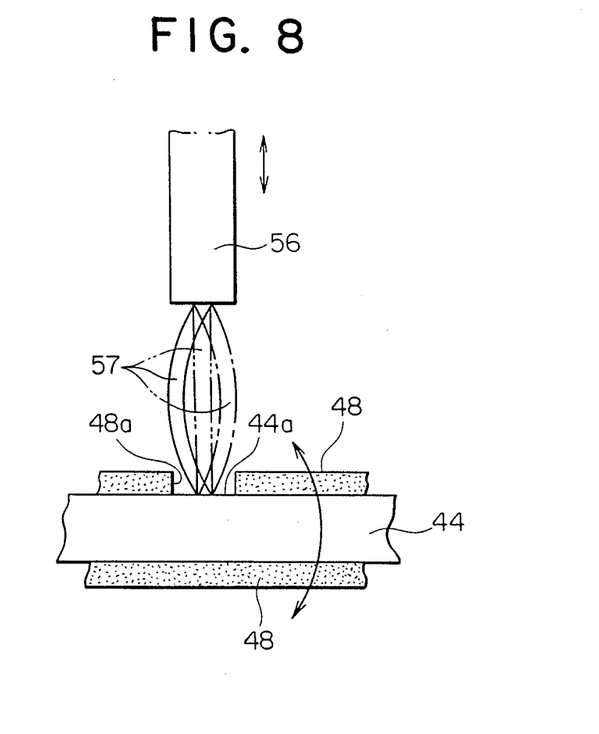
FIG. 8 is an enlarged partial sectional view of an assembly of a vibration plate and a flexible strip in the apparatus shown in FIG. 6.

As shown in FIG. 8, the lower end of the elastic strip 57 may be fastened to the exposed surface portion of the flexible plate 44 through an opening 48a formed in the upper piezoelectric element layer 48 for example by using a welding or other suitable fastening means.

Figure 9:
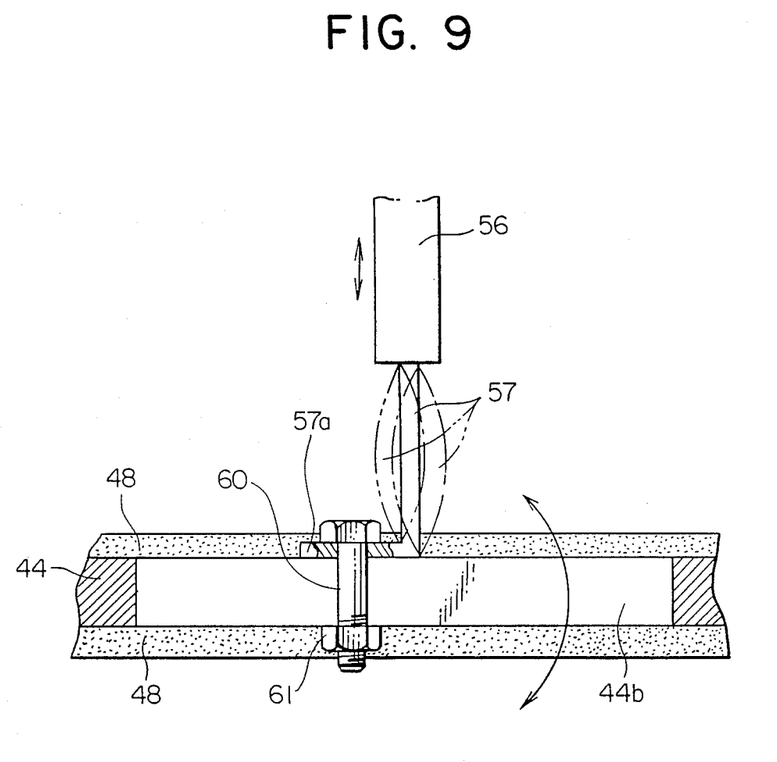
FIG. 9 is a similar view to that of FIG. 8 showing a modification of the assembly of FIG. 8.

Alternatively, as illustrated in FIG. 9, the lower end portion of the elastic strip 57 may be folded in a L-shape, and the L-shaped folded portion or seat portion 57a may be fastened to the exposed surface portion of the flexible plate 44 by using a welding or other fastening means.

In order to be able to adjust the position of the elastic strip 57 with respect to the flexible plate 44, as shown in FIG. 9, each of the upper and lower piezoelectric element layers 48 may be divided into two portions in a direction parallel to the plane of the drawing, and the exposed elongate portion of the flexible plate 44 between the divided layer portions is formed with a slot 44b which extends along the axis thereof. By inserting a bolt 60 into the slot 44b and fastening the bolt 60 with a nut 61 the L-shaped seat portion 57a of the elastic strip 57 may be movably secured to the flexible plate 44. In this case, it is necessary to make the vibration plate assembly 43 movable in a direction parallel to the plane of the drawing with respect to the table 41 so that the through hole 50a formed in the lower frame 50 is aligned with the securing position of the elastic strip 57. For this end, the flexible plate 44 may be formed with slots through which the fastenings 45 are penetrated, each slot being extended in a direction parallel to the plane of the drawing so that the flexible plate 44 is movably positioned with respect to the fastenings 45.

Referring again to FIG. 6, a load cell 62 is suspended from the upper frame 51 by two supporting rods 63. Spring 64 is fitted on the portion of the respective supporting rod 63 between the head of the rod and the upper surface of the upper frame 51. Each spring 64 is adapted to force the load cell 62 upward. The load cell 62 is provided with a sample pusher 65 which is adapted to make contact with the upper surface of the sample 59 at the intermediate point between the supporting pieces 58 provided on the sample supporting member 53.

The upper frame 51 also is provided with a threaded hole 51a at the position aligned with the through hole 50a, into which a lifting screw 66 is engaged. This lifting screw 66 has a top end provided with a handle 67, and the lower end thereof is intended to abut on the upper surface of the load cell 62. The lifting screw 66 is lowered against the springs 64 by operating the handle 67.

Then, the operation of the illustrated apparatus will be described.

As in the embodiment described with reference to FIGS. 1 to 3, the sample 59 of ceramic materials is placed on the sample supporting pieces 58 and 58 of the supporting member 53, and the lifting screw 66 is operated by the handle 67 to lower the load cell 62 until the sample pusher 65 comes into contact with the sample 59. Thus, the sample 59 is to be supported in three points. If the lifting screw 66 is lowered slightly over the suitable level for which it is intended, the elastic supporting members 42 fixed to the table 41 are compressed so that the table 41 and then the vibrating plate assembly 43 are displaced downwards resulting in the sample 59 being always retained at a constant pressure without any danger of damage. Then, the piezoelectric element layers 48 are energized by applying an alternating voltage having a predetermined frequency of a pulse wave, a sinusoidal wave or a triangular wave from the power source thereto.

Therefore, a strain shall occur in each piezoelectric element layer 48, and thus a bending vibration shall be generated in the vibration plate assembly 43, this bending vibration including a horizontal vibrating component and a vertical vibrating component. The horizontal vibrating component may be eliminated by means of the flexion of the elastic strip 57 as shown in FIGS. 8 and 9, and then only the vertical vibrating component is transmitted to the sample supporting member 53 through the interconnecting rod 56, thereby resulting in the sample supporting member 53 and then supporting pieces 58 being upwards and downwards displaced to push the end portions of the underside of the sample 59. As a result, a bending strain is periodically applied to the sample 59 with center at the position corresponding to the pusher 65. By the periodical application of the bending strain or dynamic load the sample 59 becomes fatigued and finally broken or cracked. By measuring the time until the sample 59 becomes broken, the applied voltage, the number of the pulses or other parameters encountered, the strength or other physical properties of the sample can be determined.

The present invention may conveniently be applied for a three point bending test, but may also be applied for other type test in which the sample is supported at the periphery thereof and the center of the sample is pushed.

In the preceding embodiment, it should be understood that the flexible plate 44 may be retained in two points and may be provided with weights at the both ends thereof as in the case shown in FIGS. 4 and 5.

In this case, there may be obtained a better bending vibration for the sample.

According to the cyclic fatigue testing apparatus, since the sample of the ceramic material is subjected to the dynamic load which is generated by the bending strain of the flexible plate provided with the piezoelectric element layers at the both sides thereof, it is possible to freely change the test conditions such as the magnitude and cycle of a cyclic stress to be applied by selecting the alternating voltage which is applied to the piezoelectric element layers.

As compared with the conventional system in which a mechanical reciprocating actuator mechanism is used for applying a dynamic load to a sample, the present invention can provide a system which can be operated with a little noise and a little wear due to a low mechanical friction being generated. Therefore, the same test condition can be easily maintained during the test procedure and thus there can be obtained accurate and reproducible test results.

Further, since the apparatus of the present invention utilizing the piezoelectric element has a high responsibility of the order of $\mu$ sec, a fatigue testing with a high frequency (100~1 kHz) can be performed, and thus the actual testing procedure can be run much more quickly.

The terms and expressions which have been employed herein are used as terms of description and not of limitation, and there is no intention, in the use of such terms and expressions, of excluding any equivalents of the features shown and described but it is recognized that various modifications are possible within the scope of the invention claimed.

What is claimed is:

1. A cyclic fatigue testing apparatus for testing the cyclic fatigue of samples such as ceramic, comprising a vibration plate assembly having a flexible plate provided with a piezoelectric element layer on at least one surface thereof, at least one end portion of said flexible plate being secured to a stationary table, a supporting member mounted on the bending surface of said vibration plate assembly for supporting the sample, and means for forcing the sample onto the supporting member.

2. An apparatus as claimed in claim 1, wherein said flexible plate of the vibration plate assembly is secured to said table at one end portion and is provided with a weight at the other end portion.

3. An apparatus as claimed in claim 1, wherein said flexible plate of the vibration plate assembly is secured to said table at the both end portions which have outwardly extended edges on which the weights are mounted, respectively.

4. An apparatus as claimed in claim 1, wherein said stationary table is provided with elastic supporting means for compensating any overload applied by said loading means to the sample.

5. An apparatus as claimed in claim 1, wherein said sample supporting member is adjustably positioned with respect to said flexible plate of the vibration plate assembly.

6. A cyclic fatigue testing apparatus for testing the cyclic fatigue of samples such as ceramic, comprising a vibration plate assembly having a flexible plate provided with a piezoelectric element layer on at least one surface thereof, at least one end portion of said flexible plate being secured to a stationary table, a supporting member for supporting the sample, means for liftably retaining said sample supporting member, an elastic strip member for interconnecting said sample supporting member and the bending surface of said vibration plate assembly, and means for forcing the sample onto said sample supporting member.

7. An apparatus as claimed in claim 6, wherein said flexible plate of the vibration plate assembly is secured to said table at one end portion and is provided with a weight at the other end portion.

8. An apparatus as claimed in claim 6, wherein said flexible plate of the vibration plate assembly is secured to said table at the both end portions which have outwardly extended edges on which the weights are mounted, respectively.

9. An apparatus as claimed in claim 6, wherein said stationary table is provided with elastic supporting means for compensating any overload applied by said loading means to the sample.

10. An apparatus as claimed in claim 6, wherein said sample supporting member is adjustably positioned with respect to said flexible plate of the vibration plate assembly.

11. An apparatus as claimed in claim 6, wherein said elastic strip member has one end secured to the bending surface of said vibration plate assembly and other end connected to the underside of the sample supporting member through an interconnecting rod which passes through a hole provided in said retaining means.

* * * * *